(12) United States Patent
Geyer et al.

(10) Patent No.: US 7,172,990 B2
(45) Date of Patent: Feb. 6, 2007

(54) HIGHLY ACTIVE SPHERICAL METAL SUPPORT CATALYSTS

(75) Inventors: Reinhard Geyer, Halle (DE); Rainer Schödel, Teutschenthal (DE); Peter Birke, Langenbogen (DE); Jürgen Hunold, Halle (DE)

(73) Assignee: Shell Internationale Research Maatschappiji, B.V., Hague (NL)

( * ) Notice: Subject to any disclaimer, the term of this patent is extended or adjusted under 35 U.S.C. 154(b) by 576 days.

(21) Appl. No.: 10/346,993

(22) Filed: Jan. 17, 2003

(65) Prior Publication Data

US 2004/0220436 A1 Nov. 4, 2004

(30) Foreign Application Priority Data

Jan. 22, 2002 (DE) .................. 102 02 127

(51) Int. Cl.
- *B01J 23/00* (2006.01)
- *B01J 21/00* (2006.01)
- *B01J 20/00* (2006.01)
- *B01J 35/00* (2006.01)

(52) U.S. Cl. .................. 502/326; 502/104; 502/107; 502/110; 502/111; 502/113; 502/117; 502/118; 502/84; 502/235; 502/237; 502/238; 502/240; 502/244; 502/245; 502/252; 502/253; 502/257; 502/258; 502/259; 502/260; 502/324; 502/327; 502/328; 502/329; 502/330; 502/331; 502/332; 502/335; 502/336; 502/337; 502/338; 502/340; 502/341; 502/342; 502/343; 502/344; 502/345; 502/346; 502/355; 502/415; 502/439

(58) Field of Classification Search .................. 502/104, 502/107, 110, 111, 113, 117, 118, 84, 235, 502/237, 238, 240, 244, 245, 252, 253, 257–260, 502/324, 326–332, 335–338, 340–346, 355, 502/415, 439

See application file for complete search history.

(56) References Cited

U.S. PATENT DOCUMENTS

| | | | |
|---|---|---|---|
| 3,495,954 A | | 2/1970 | Grimes et al. |
| 3,776,987 A | | 12/1973 | Grimes et al. |
| 3,826,755 A | * | 7/1974 | McKenna et al. .......... 252/635 |
| 3,849,545 A | * | 11/1974 | Miklas .................. 423/594.2 |
| 3,887,491 A | * | 6/1975 | Ramirez et al. ............ 502/159 |
| 3,937,667 A | | 2/1976 | Scott et al. |
| 4,206,078 A | * | 6/1980 | Ohorodnik et al. ......... 502/181 |
| 4,397,770 A | * | 8/1983 | Cairns et al. .............. 502/316 |
| 4,571,315 A | | 2/1986 | Gerontopoulos et al. |
| 6,251,823 B1 | * | 6/2001 | Yamaguchi et al. ........ 502/439 |
| 6,495,488 B2 | * | 12/2002 | Yamaguchi et al. ........ 502/238 |
| 6,677,271 B1 | * | 1/2004 | Birke et al. ................ 502/337 |
| 2001/0012816 A1 | | 8/2001 | Yamaguchi et al. |

FOREIGN PATENT DOCUMENTS

| | | |
|---|---|---|
| CH | 566809 | 9/1975 |
| DE | 198 30 795 A1 | 1/2000 |
| EP | 0 479 553 B1 | 4/1995 |
| GB | 1462049 | 1/1977 |
| WO | WO 00/02830 | 1/2000 |

* cited by examiner

*Primary Examiner*—Cam N. Nguyen
(74) *Attorney, Agent, or Firm*—Bateman IP Law Group

(57) ABSTRACT

The invention relates to highly active spherical metal support catalysts with a metal content of 10 to 70% by mass, and a process for their production with the use of a mixture of polysaccharides and at least one metal compound which is dropped into a metal salt solution.

24 Claims, No Drawings

HIGHLY ACTIVE SPHERICAL METAL SUPPORT CATALYSTS

RELATED APPLICATIONS

The present application claims priority to German Patent Application 10202127.9, filed Jan. 22, 2002.

BACKGROUND

The invention relates to spherical metal support catalysts, a process for their production, and a process for the hydrogenation of aromatic substances.

In the use of catalysts in fixed-bed reactors, the spherical form of the catalysts leads to a uniform packing of the catalyst bed and thereby to the avoidance of undesired channels.

The production of spherical catalysts is sufficiently described in the literature. Numerous examples for the production of oxidic substrates by the application of the dropping of hydrosols into various solutions are protected: U.S. Pat. No. 4,198,318 describes the production of spherical $Al_2O_3$ substrates by the dropping of an acidic hydrosol into an aqueous ammonia solution in the presence of a non-ionic surface-active agent. In DE 403 5089 the dropping is accomplished by a vibrating nozzle plate. US 2001/0012816 A1 describes the dropping of mixtures of polysaccharide solutions with hydrated $Al_2O_3$, $SiO_2$ $Al_2O_3$, $ZrO_2$ $Al_2O_3$, or $TiO_2$ $Al_2O_3$ gels or with $Al_2O_3$, $B_2O_3$ $Al_2O_3$ or $B_2O_3$ $SiO_2$ $Al_2O_3$ hydrates in an aqueous solution of $Ca^{2+}$, $Al^{3+}$, $Mg^{2+}$, $Ba^{2+}$ or $Sr^{2+}$ ions.

All dropping processes described previously are, however, based solely upon oxidic substrates. Dropping processes for the production of metal support catalysts with a metal content>10% by mass, which must be reduced after the dropping, drying, and possible calcination, have not been described previously.

A further method for the production of spherical catalysts is the granulation process, which however does not lead to a uniform spherical size. Further disadvantages of this process are the rough surface of the spheres as well as the irregular distribution of pore sizes over the cross-section of the sphere.

Furthermore, spherical catalysts are made with the use of "spheronizers." Therein, formed pieces already produced are formed into spheres on a rotating plate, as, for example, is described for oxidic substrates in WO 99/58236. In these processes, the porosity is pre-determined in large part in the forming into extrudates, and the uniformity of the spherical size and the spherical shape is, moreover, unsatisfactory.

SUMMARY OF THE INVENTION

Thus, the present invention is based on the technical problem of providing highly active metal support catalysts for hydrogenation processes which have a uniform spherical size and spherical shape as well as a high metal dispersity, a high porosity, and a uniform distribution of pore sizes.

The present invention is also based on the technical problem of providing processes for the production of such catalysts.

DETAILED DESCRIPTION

This technical problem is solved according to the invention by the fact that a process for the production of formed spherical metal support catalysts with a metal content of 10 to 70% by mass is provided, wherein a mixture of at least one polysaccharide and at least one iron, cobalt, nickel, copper, or zinc compound of the group of metal oxides, metal hydroxides, basic metal carbonates, metal hydrogen carbonates, metal silicates, metal zirconates, metal aluminates, metal titanates, metal chromites, or metal aluminosilicates, dissolved or suspended in a liquid medium, is dropped into a metal salt solution, whose metal ions are preferably also a component of the at least one selected metal compound. Compounds of other polyvalent cations such as $Mg^{2+}$, $Ca^{2+}$, $Sr^{2+}$, $Ba^{2+}$, $Mn^{2+}$, $Al^{3+}$, and $Cr^{3+}$ are, according to the invention, preferably used as a metal salt solution. The spherically formed pieces of catalyst obtained in this metal salt solution from the mixture are separated from it after a standing time of 1 to 180 minutes and then dried at temperatures of 80 to 150° C. and reduced at temperatures of 150 to 600° C. Subsequently, the formed pieces of catalyst are preferably stabilized in a manner which is known per se.

Through the process according to the invention, spherically formed pieces of catalyst are obtained which have a very uniform spherical shape. The catalysts obtained with the process according to the invention have in addition a most highly uniform particle size.

With respect to the catalyst obtained by processes according to the state of the art, the catalyst obtained according to the process according to the invention show a clearly increased volume of pores with distinctly more macropores above 50 nm. The high proportion of macropores leads, according to the invention, to a speedier discharge of the reduction water from the formed pieces of catalyst. A particular advantage of the process according to the invention thus also consists of the greatly increased metal dispersities of the reduced catalysts.

A further advantage of the formed pieces of catalyst obtained according to the invention consists of the increased mechanical strength with, the same time, increased pore volume after the reduction.

Through the choice of at least one iron, cobalt, nickel, copper, or zinc compound in the mixture and/or through the solid ratio of this compound to the at least one added polysaccharide, the pore structure of the obtained catalyst according to the invention can be set as desired. Preferred according to the invention are solid ratios (relative to the ignition residue) of 4 to 15, in particular of 4.4 to 8.5. According to the invention, alginate is preferred as the polysaccharide. According to the invention, water is preferably used as the liquid medium.

In a preferred form of embodiment, the mechanical strength of the spheres is increased by at least one solid and/or liquid aggregate material, which is added to the at least one iron, cobalt, nickel, copper, or zinc compound, preferably before the dropping, and which acts as a binding agent. According to the invention, preferably at least one of the following aggregate materials is used: tylose, bentonite, boehmite, kaolin, silica gel, methyl cellulose, silica sol, and silicate of sodium. Preferred according to the invention are solid ratios (relative to the ignition residue) of the at least one iron, cobalt, nickel, copper, or zinc compound to the at least one aggregate material of 4 to 15, in particular of 10 to 12. In a variant the pore structure of the obtained catalyst according to the invention can be set as desired through amount and type of aggregate material.

The mechanical strength of the catalyst obtained is preferably determined according to the invention through the type and concentration of the at least one metal ion in the metal salt solution, in particular in a dropping column.

According to the invention, iron salt solutions are preferably used for iron support catalysts, cobalt salt solutions are preferably used for cobalt support catalysts, nickel salt solutions are preferably used for nickel support catalysts, copper salt solutions are preferably used for copper support catalysts, and zinc salt solutions are preferably used for zinc support catalysts. The metal salt solutions can also contain other polyvalent metal ions or mixtures of these, in particular, the metals magnesium, calcium, strontium, barium, manganese, aluminum, or chromium, such as $Mg^{2+}$, $Ca^{2+}$, $Sr^{2+}$, $Ba^{2+}$, $Mn^{2+}$, $Al^{3+}$ or $Cr^{+3+0.}$ In a preferred form of embodiment, the at least one metal salt is present as metal nitrate and/or metal acetate in the aforementioned metal salt solution. In a variant of this preferred form of embodiment, the at least one metal salt is present in an amount of 0.3 to 5% by mass, preferably from 1 to 2% by mass in the metal salt solution.

In a further preferred form of embodiment, at least one doping element from the magnesium, calcium, manganese, molybdenum, chromium, iron, and zinc group is added in addition to the metals iron, cobalt, nickel, copper and/or zinc in an amount of 0.1 to 5% by mass, preferably from 1 to 3% by mass. In a particularly preferred form of embodiment, manganese in an amount of 2% of mass is used for doping.

In a further preferred form of embodiment the spherical formed pieces of catalyst obtained in the metal salt solution during the production of catalyst are separated from it after a dwelltime of from 1 to 180 minutes, subsequently dried at temperatures of from 80 to 150° C., and thereafter calcined at temperatures of 150 to 600° C. before they are reduced at temperatures of 150 to 600° C.

Preferably the reaction management of the reduction and stabilization of the dried or calcined catalysts according to the state of the art is performed as presented, by way of example, in the embodiment examples.

In this connection an additional object of the present invention is a spherical metal support catalyst with the aforementioned properties, which can be obtained by a process according to the invention.

In this connection an additional object of the present invention is a process for the hydrogenation of preferably substituted and/or unsubstituted aromatic substances and/or mixtures thereof which are liquid or gaseous where these aromatic substances are hydrogenated with the use of the metal support catalyst which can be obtained by a process according to the invention.

In connection with the present invention, additional advantages and additional variants of embodiment follow from the embodiment examples below where the features explained can be applicable not only in the specified combinations but rather also in other combinations or alone.

EXAMPLE 1

(According to the Invention):

0.6 l of water are placed in an agitating container and thereafter 9 g of sodium alginate are added. After the alginate has dissolved completely, 5.7 g of silicon dioxide, in the form of a silicate of sodium solution with a concentration of 190 g $SiO_2$/l of solution, are added while stirring. The solution obtained is stirred for 5 minutes more and following this 200 g of a nickel-silicon dioxide metal compound with an ignition residue (2 hours at 800° C.) of 20% by mass (corresponding to 40 g solid relative to ignition residue) is added into the solution.

The ratio of metal compound (relative to the ignition residue) and to the alginate used (solid) in the mixture is 4.4, the metal compound/aggregate material ratio is 7.

For the production of a free-flowing suspension, the mixture (slurry) is then homogenized with the use of an Ultraturrax for 5 minutes (500 rpm) and thereafter pumped continuously into a ceramic dropping head provided with slots (3 mm in diameter) (full volume ca. 300 ml) and dropped therefrom.

The dropping of the solution is done into a liquid column which contains an aqueous nickel nitrate solution (1% nickel). The distance between dropping head and liquid surface is about 10 cm, the total solution volume is 1.5 l. Immediately after immersion of the drops into the nickel solution, the gel formation occurs. The uniformly shaped spheres are deposited at the base of the container. After the dropping has been completed the material thus produced is left another 30 minutes for complete hardening in the solution.

Thereafter, the solution is decanted and the catalyst particles formed are washed with ca. 5 l of pure condensate.

Immediately thereafter, the drying of the formed pieces is done at 130° C. for 15 hours. After the drying the spherical catalyst material has a very uniform shape and size.

The dried catalyst is thereafter calcined in a suitable integral reactor in a nitrogen stream at temperatures of ca. 350° C. and, after conversion to hydrogen (gas load ca. 2000 v/vh), reduced for 6 hours at temperatures of 400° C.

The stabilization of the pyrophoric catalyst is done thereafter with the use of an air/nitrogen mixture (beginning with $O_2$ concentrations of 0.1% by volume to 2% by volume).

Obtained therefrom, the catalyst according to the invention contains 58% nickel and has a degree of reduction of 75%. The nickel metal surface (determined by CO chemisorption) is 50 $m^2$/g of catalyst, the average nickel crystallite size is 3 nm, and the apparent settled density is 0.5 kg/l.

The catalyst according to the invention has furthermore an outstanding uniformity of its particle size distribution. The average diameter is 2.15 nm. All the catalyst particles have a diameter of 2.0 to 2.3 mm.

The characteristic data of the mechanical and physical-chemical characterization of the catalyst produced according to the invention are summarized in Table 2. From this it can be seen that the catalyst obtained is distinguished by an extremely high pore volume with, at the same time, appropriate strength of the formed pieces of catalyst.

EXAMPLE 2

(According to the Invention):

In 0.6 l of water, 6 g of sodium alginate are dissolved while stirring and subsequently 3.5 g of silicon dioxide in the form of a silica sol solution with a concentration of 498 g $SiO_2$/l of solution are added. After about 5 minutes 60 g of a spray-dried powdered catalyst intermediate product with an ignition residue (2 hours 800° C.) of 75% (corresponding to 45 g solid relative to ignition residue) are added, said catalyst intermediate product being produced in a manner known per se by joint precipitation of nickel, aluminum oxide, and silicon dioxide with NaOH.

The powder used has a density of ca. 0.3 kg/l and an average grain size of ca. 8 μm.

The ratio of metal compound (relative to the ignition residue) and to the alginate used (solid) in the mixture is 7.5. The metal compound-aggregate material ratio is 13.

After homogenization of the suspension by means of an Ultraturrax, the suspension is dropped into an aqueous nickel acetate solution (5% nickel) as in example 1. The dropped material remains in the nickel acetate solution for 15 minutes.

After separation of this solution, the formed pieces of catalyst are then dried and subsequently, without calcination in a hydrogen stream, reduced in a hydrogen stream at temperatures of 380° C.

The stabilization of the pyrophoric catalyst is done in the nitrogen/air/carbon dioxide mixture in a manner known per se. The $CO_2$, content in the gas mixture is 1% by volume.

Obtained therefrom, the catalyst according to the invention contains 55% nickel and has a degree of reduction of 60%. The nickel metal surface (determined by CO chemisorption) is 33 $m^2$/g of catalyst, the average nickel crystallite size is 2.7 nm, and the apparent settled density is 0.4 kg/l.

The catalyst obtained has furthermore an outstanding uniformity of it particle size distribution with an average diameter is 2.6 nm. In the process, all the catalyst particles have a diameter of 2.4 to 2.8 mm.

The results of the mechanical and physical-chemical characterization of the catalyst 2 according to the invention are also presented in Table 2. It can be seen that the catalyst is also distinguished by an extremely high pore volume with good strength of the formed pieces.

EXAMPLE 3

(According to the Invention):

In 0.6 l of water, 12 g of sodium alginate is dissolved while stirring and subsequently mechanical mixing, consisting of 80 g of a customarily produced powdered, dried, and calcined nickel-aluminum oxide precipitate catalyst and 8 g of a Böhmite (Versal 250 from the UOP Co., ignition residue 74.7%, corresponding to 6 g of solid, relative to the ignition residue) is added. The oxidic catalyst starting material has an apparent settled density of 0.8 kg/l and an average grain size of 10 μm.

The ratio of metal compound (relative to the ignition residue) and to the alginate used (solid) in the mixture is 6, the metal compound/aggregate material ratio is 12.

The production of the catalyst suspension which can be dropped is done in the way specified in Example 1. The dropping of the solution is carried out in a 3% nickel nitrate solution. In so doing, the dropped catalyst particles have a very uniform shape and size.

After drying and calcination of the catalyst material taken, the reduction is carried out at 420° C. in a hydrogen stream. The stabilization of the catalyst spheres is done under the conditions described in Example 1.

The obtained catalyst according to the invention contains 65% nickel and has a degree of reduction of 70%. The nickel-metal surface (determined by means of CO chemisorption) is 28 $m^2$/g catalyst, the nickel crystallite size is 3.7 nm, and the apparent settled density is 0.75 kg/l.

The obtained catalyst has furthermore a good uniformity in its particle size distribution. The average particle diameter is 2 mm. All the catalyst particles have a diameter of 1.9 to 2.2 mm.

The results of the mechanical and physical-chemical characterization of the catalyst 3 according to the invention are represented in Table 2.

EXAMPLE 4

(According to the Invention):

In 0.6 l of water, 9 g of sodium alginate is dissolved while stirring and subsequently 8 g of a commercially available silica sol with an ignition residue of 90% is added. Thereafter, the dosing of 80 g of a powdered, dried, and calcined cobalt-manganese-titanium oxide-precipitate catalyst with an ignition residue of ca. 95%, corresponding to 76.5 g of solid relative to the ignition residue. The powdered starting material lies, with regard to grain size, entirely below 63 μm. The density is 0.8 kg/l.

The ratio of metal compound (relative to the ignition residue) and to the alginate used (solid) is 8.5. The metal compound-aggregate material ratio is 10.6.

The production of the catalyst suspension which can be dropped is done in the way specified in Example 1. The dropping of the catalyst slurry is carried out in a 1.5% calcium nitrate solution. In the process, the dropped catalyst particles have a very uniform and round shape.

After drying and calcination of the catalyst material obtained, it has a cobalt content of 30% and a manganese content of 2%.

The catalyst according to the invention is reduced before its catalytic evaluation for the hydrogenation of substituted aromatic substances at temperatures of 400° C. and stabilized in the customary way.

It has with a small particle size distribution an average particle size of 2.1 mm. In the process, all the catalyst particles have a diameter of 1.8 to 2.2 mm.

EXAMPLE 5

(According to the Invention):

In 0.3 of an aqueous silicate of sodium solution with an $SiO_2$ content of 61 g/l solution corresponding to 18.3 g $SiO_2$, 100 g of a spray-dried copper silicon dioxide precitate catalyst with an ignition residue of 73.5% (corresponding to 73.5 g solid relative to the ignition residue) are added while stirring. Thereafter, 300 g of a 2% sodium alginate solution, corresponding to 6 g alginate, are added.

The ratio of metal compound (relative to the ignition residue) and alginate used solid in the mixture is 12.25, the metal compound-aggregate material ratio is 4.

After homogenization of the suspension, it is heated to 60° C. while stirring and treated at this temperature for ca. 15 minutes. After cooling of the homogeneous suspension and subsequent treatment with the Ultraturrax, the dropping into a 3% copper nitrate solution takes place. After conclusion of the dropping, the spherical catalyst particles remain in the copper nitrate solution for another 10 minutes.

After separation of the copper nitrate solution and washing of the obtained catalyst material, the drying and calcination take place.

The obtained catalyst according to the invention has an average particle size of 2 mm and is distinguished by a uniform size and shape.

Following the calcination, the catalyst is reduced in a nitrogen/hydrogen stream (2% $H_2$) at temperatures of 200° C. and subsequently stabilized according to Example 1.

The finished catalyst contains 65% copper and has a degree of reduction of 70%. The average copper primary particle size is 8.7 nm.

The catalyst according to the invention has furthermore a good uniformity of the particle size distribution. All the catalyst particles have a diameter of 1.8 to 2.1 nm, the average particle diameter is 1.9 mm, and the apparent settled density is 0.4 kg/l.

EXAMPLE 6

(Comparative Catalyst):

Dried and milled nickel/SiO$_2$ starting material with an average grain size of 10 μm and an apparent settled density of 0.7 kg/l is mixed with tylose as binding agent and subsequently peptized in a laboratory kneader with the addition of condensate water, nitric acid, and silica sol solution. The tylose addition is 2.5% relative to the solid content of the kneaded batch. After a kneading time of 15 minutes, the complete batch is formed into 3-mm full extrudates in a laboratory extruder with cutting apparatus.

The moist extrudates obtained are then processed into spheres in a laboratory spheronizer (Caleva Co. Model 120, England). Following this, the spherical material obtained is dried at 130° C. and has the grain spectrum represented in Table 1.

TABLE 1

| Grain size (mm) | % by Mass |
|---|---|
| >5 | — |
| 4–5 | 0.1 |
| 3–4 | 10.7 |
| 2.5–3.0 | 39.9 |
| 2.0–2.5 | 25.8 |
| 1.6–2.0 | 16.1 |
| 1.0–1.6 | 7.4 |
| <1.0 | — |

Along with the very broad grain spectrum the catalyst particles have a uniform and in part non-uniform spherical shape.

The catalyst material obtained is subsequently reduced at 400° C. in a hydrogen stream and stabilized under standard conditions known per se.

The comparative catalyst obtained contains 55% nickel and has a degree of reduction of 75%. The nickel metal surface (determined by CO chemisorption) is 30 m$^2$/g catalyst, the average nickel crystallite size is 4.5 nm, and the apparent settled density is 0.8 kg/l.

The catalyst shows a broad particle size distribution with diameters of 2 to 4 mm.

Additional characteristic data of the physical-chemical characterization of the comparative catalyst obtained are contained in Table 2. It can be seen that the comparative catalyst has a clearly smaller pore volume with clearly fewer macropores above 5 nm with respect to the catalyst produced according to the invention.

EXAMPLE 7

(Comparative Catalyst):

The cobalt-manganese-titanium dioxide catalyst starting material dried and calcined according to Example 4 is formed with the addition of graphite into 3 mm×3 mm tablets. Following the forming, the catalyst material is reduced and stabilized as described in Example 4.

The finished catalyst has an apparent settled density of 1.2 kg/l and a crush strength of 35 Mpa.

The results of the mechanical and physical characterization of the comparative catalyst are summarized in Table 2.

EXAMPLE 8

(Comparative Catalyst):

The copper-silicon dioxide catalyst starting material used in Example 5 is calcined at 350° C. and subsequently peptized with the addition of tylose, condensate water, and nitric acid in a suitable mixing unit and subsequently formed into 1.6 mm trilobe extrudates. After drying and calcination of the formed pieces, the reduction and stabilization of the starting material takes place under the conditions described in Example 5.

The finished catalyst contains 70% copper and has a degree of reduction of 75%. The apparent settled density is 0.85 kg/l, the copper crystallite 09.2 nm.

EXAMPLE 9

(Comparative Catalyst):

For catalytic evaluation, a commercially available spherical nickel-alumosilicate catalyst with the following physical-chemical characteristic data is drawn upon:

| | |
|---|---|
| Nickel content (% by mass) | 55 |
| Nickel degree of reduction (%) | 60 |
| Apparent settled density (kg/l) | 0.95 |
| Average particle diameter (mm) | 2.5 |
| Particle diameter range (mm) | 1.6–4.7 |
| Nickel crystallite size (nm) | 5.1 |

Along with the very broad distribution of particle size, this catalyst has a very non-uniform spherical shape. Thus, it contains along with spherical particles of different size, also extrudates and broken pieces of extrudates. Table 2:

Physical-chemical and mechanical characteristic data of the catalysts produced according to the invention and the comparative catalysts

| Catalyst | Apparent settled density (kg/l) | Abrasion* (%) | Total pore volume (cm$^3$) | Pore volume >50 nm (cm$^3$/g) |
|---|---|---|---|---|
| 1 (invent.) | 0.5 | 0.8 | 0.84 | 0.52 |
| 2 (invent.) | 0.4 | 1.0 | 0.95 | 0.64 |
| 3 (invent.) | 0.75 | 0.7 | 0.60 | 0.29 |
| 4 (invent.) | 0.5 | 0.3 | 0.45 | 0.29 |
| 5 (invent.) | 0.4 | 1.2 | 0.82 | 0.58 |
| 6 (comp.) | 0.8 | 0.55 | 0.30 | 0.02 |
| 7 (comp.) | 1.2 | 0.5 | 0.27 | 0.14 |
| 8 (comp.) | 0.85 | 1.2 | 0.30 | 0.07 |
| 9 (comp.) | 0.95 | 0.8 | 0.35 | 0.04 |

*Standard abrasion test (Roll test, 25 g catalyst, 40 rpm, 30 min)

EXAMPLE 10

(Hydrogenation of Aromatic Substances with Nickel Support Catalysts):

For the catalytic characterization of the nickel support catalysts according to Examples 1 to 3 in comparison to the comparative catalysts according to Examples 6 to 9, the hydrogenation of aromatic substances in kerosene in the fixed-bed process by means of an integral-flow reactor (inner diameter: 25 mm) is used.

The catalyst volume installed is 50 ml. The 50 ml catalyst volume is installed in 10 portions with 10 portions of SiC in the volume ratio of 1:1.

Before the catalytic reaction the catalysts are reactivated in a hydrogen stream (50 l/h) over a time period of 4 hours at 250° C. A kerosene with a content in aromatic substance of 18% by mass and a sulfur content of 1.1 ppm is used as feed. The reaction conditions are:

| | |
|---|---|
| Reaction pressure | 30 bar |
| Reaction temperature | 85°      100° C. |
| Reaction time | 40 h      80 h |
| LHSV | 1.3 ml/ml · h |
| Gas product-volume ratio $H_2$/kerosene | 400:1 |

The results are summarized in Table 3.

TABLE 3

| | Reaction temperature 85° C. Aromatic fraction in reaction product (ppm) | Reaction temperature 100° C. Aromatic fraction in reaction product (ppm) |
|---|---|---|
| 1 (invent.) | 1600 | 150 |
| 2 (invent.) | 1750 | 160 |
| 3 (invent.) | 1550 | 152 |
| 6 (comp.) | 2640 | 259 |
| 9 (comp.) | 3105 | 298 |

A comparison of measurement results of catalytic hydrogenation makes clear the advantage of the catalysts according to the invention: The degree of hydrogenation or decomposition of aromatic substances is significantly greater with the catalysts according to the invention than with the conventional catalysts.

EXAMPLE 11

(Hydrogenation of Aromatic Substances with Cobalt-manganese Support Catalysts):

The cobalt-manganese-titanium dioxide catalyst (Example 4) is tested catalytically in the hydrogenation of isocamphyl pyrocatechine to sandal alcohols. As comparative catalyst, a catalyst in the form of a pill (Example 7) of the same composition is tested.

The catalytic test is performed in the fixed-bed process by means of an integral-flow reactor (inner diameter 25 mm). A catalyst volume of 50 ml is used. The 50 ml catalyst volume is installed in 10 portions with 10 portions of SiC in the volume ratio of 1:1.

Before the catalytic reaction, the catalysts are reactivated in a hydrogen stream (50 l/h) over a time period of 3 hours at 300° C. A mixture of isocamphyl pyrocatechine and cyclohexanol (1:1) is used as feed. The additional reaction conditions are:

| | |
|---|---|
| Reaction pressure | 70 bar |
| Reaction temperature | 220° C. |
| Reaction time | 50 h |
| LHSV (isocamphyl pyrocatechine) | 0.5 ml/ml · h. |
| Gas product-volume relationship $H_2$/isocamphyl pyrocatechine | 4000:1 |

The catalytic measurement results are given in Table 4.

TABLE 4

| Catalyst | Catalyst form pore radii | Yield on sandal alcohol (%) | Yield on hydrocarbons (%) |
|---|---|---|---|
| 4 (invent.) | Spherical 2.1 mm | 82.1 | 7.9 |
| 7 (comp.) | Tablet 3 mm | 68.9 | 10.8 |

The results show that, with the same chemical composition, the catalyst according to the invention has a higher activity and a higher selectivity than the catalyst in the form of a strand.

EXAMPLE 12

(Hydrogenation of Aromatic Substances with Copper Support Catalysts):

With the same reactor system as in Example 11, the catalytic characterization of copper-silicon dioxide catalyst (Example 5) is also performed in the acetophenone hydrogenation. The catalyst from Example 8 serves as a comparative catalyst. A mixture of 70% by mass of acetophenone and 30% by mass of methyl-phenyl carbinol is used as feed. The additional reaction conditions are:

| | |
|---|---|
| Reaction pressure | 20 |
| Reaction temperature | 80° C. |
| Reaction time | 40 h |
| LHSV (isocamphyl pyrocatechine) | 0.5 ml/ml · h. |
| Gas product-volume ratio $H_2$/feed | 250:1 |

The catalytic measurement results are summarized in Table 5.

TABLE 5

| Catalyst | Catalyst form | Yield on methyl-phenyl carbinol (%) |
|---|---|---|
| 5 (invent.) | Spherical | 76.4 |
| 8 (comp.) | Trilobe extrudate | 66.9 |

The results show that, with the same chemical composition, the catalyst according to the invention has a higher catalytic activity than the comparative catalyst.

The invention claimed is:

1. A process for producing spherical metal support catalysts having a metal content of 10 to 70% by mass, the method comprising:
   selecting a mixture of at least one polysaccharide and at least one metal compound chosen from the group consisting of: a) metal oxides, b) metal hydroxides, c) basic metal carbonates, d) metal hydrogen carbonates, e) metal silicates, f) metal zirconates, g) metal aluminates, h) metal titanates, i) metal chromites and j) metal aluminosilicate, of iron, cobalt, nickel, copper, or zinc, dissolved or suspended in a liquid medium, and
   dropping said mixture into a metal salt solution so as to form spheres from the mixture, and forming catalyst spheres by separating the spheres from the metal salt solution after a standing time of 1 to 180 minutes, drying the spheres at temperatures of 80 to 150° C., and reducing the spheres at temperatures of 150 to 600° C.

2. The process according to claim 1, wherein the metal salt solution comprises at least one metal ion of the at least one selected metal compound.

3. The process according to claim 2, wherein the metal salt solution comprises at least one polyvalent metal ion chosen from the group consisting of $Mg^{2+}$, $Ca^{2+}$, $Sr^{2+}$, $Ba^{2+}$, $Mn^{2+}$, $Al^{3+}$ and $Cr^{3+}$.

4. The process according to claim 2, wherein the concentration of metal ions in the metal salt solution is 0.3 to 5% by mass.

5. The process according to claim 2, wherein dropping said mixture into the metal salt solution is performed from about 10 cm.

6. The process according to claim 2, wherein the metal salt solution contains nitrate and/or acetate as anions.

7. The process according to claim 2, wherein in the mixture at least one aggregate material is added which functions as a binder.

8. The process according to claim 7, wherein the aggregate material is chosen from the group consisting of tylose, bentonite, boehmite, kaolin, silica gel, silica sol, methyl cellulose and sodium silicate.

9. The process according to claim 2, wherein the at least one metal compound has an ignition residue, and wherein the solid ratio of the ignition residue of the at least one metal compound in the mixture to the at least one polysaccharide is 4 to 15.

10. The process according to claim 2, wherein one or more doping elements of 0.1 to 5% by mass is added to the mixture.

11. The process according to claim 2, wherein the catalyst spheres obtained are calcined at temperatures from 150 to 600 ° C. after the drying and before the reduction.

12. The process according to claim 1, wherein the metal salt solution consists of at least one polyvalent metal ion chosen from the group consisting of $Mg^{2+}$, $Ca^{2+}$, $Sr^{2+}$, $Ba^{2+}$, $Mn^{2+}$, $Al^{3+}$ and $Cr^{3+}$.

13. The process according to claim 1, wherein the concentration of metal ions in the metal salt solution is 0.3 to 5% by mass.

14. The process according to claim 1, wherein the concentration of metal ions in the metal salt solution is 1 to 2% by mass.

15. The process according to one of the claims 1, wherein the metal salt solution contains nitrate and/or acetate as anions.

16. The process according to one of the claims 1, wherein in the mixture at least one aggregate material is added which functions as a binder.

17. The process according to claim 16, wherein the aggregate material is chosen from the group consisting of tylose, bentonite, boehmite, kaolin, silica gel, silica sol, methyl cellulose and sodium silicate.

18. The process according to claim 17, wherein the at least one metal compound has an ignition residue, and wherein the solid ratio of the ignition residue of the at least one metal compound in the mixture to the at least one aggregate material is 4 to 15.

19. The process according to claim 1, wherein the at least one metal compound has an ignition residue, and wherein the solid ratio of the ignition residue of the at least one metal compound in the mixture to the at least one polysaccharide is 4 to 15.

20. The process according to claim 19, wherein alginate is used as the polysaccharide.

21. The process according to claim 1, wherein one or more doping elements of 0.1 to 5% by mass is added to the mixture.

22. The process according to claim 21, wherein the doping elements are Mg, Ca, Mn, Mo, Cr, Fe, or Zn.

23. The process according to claim 1, wherein the catalyst spheres obtained are calcined at temperatures from 150 to 600 ° C. after the drying and before the reduction.

24. The process according to claim 1, wherein the catalyst spheres obtained are reduced in hydrogen gas.

* * * * *